US00PP34989P3

(12) United States Plant Patent
Scalzo et al.

(10) Patent No.: US PP34,989 P3
(45) Date of Patent: Feb. 21, 2023

(54) BLUEBERRY PLANT NAMED 'C14-771'

(50) Latin Name: ***Ericaceae Vaccinium corymbosum* hybrid**
Varietal Denomination: C14-771

(71) Applicants: Costa Berry International Pty Ltd, Ravenhall (AU); FLORIDA FOUNDATION SEED PRODUCERS, INC., Marianna, FL (US)

(72) Inventors: Jessica Scalzo, Corindi Beach (AU); James W. Olmstead, Aptos, CA (US)

(73) Assignees: COSTA BERRY INTERNATIONAL PTY LTD, Revenhall (AU); FLORIDA FOUNDATION SEED PRODUCERS, INC., Marianna, FL (US)

( * ) Notice: Subject to any disclaimer, the term of this patent is extended or adjusted under 35 U.S.C. 154(b) by 0 days.

(21) Appl. No.: 17/803,049

(22) Filed: Jan. 26, 2022

(65) Prior Publication Data

US 2022/0248583 P1 Aug. 4, 2022

Related U.S. Application Data

(60) Provisional application No. 63/206,156, filed on Jan. 29, 2021.

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./156, 157
See application file for complete search history.

*Primary Examiner* — Karen M Redden
(74) *Attorney, Agent, or Firm* — Baker & McKenzie LLP

(57) ABSTRACT

The new blueberry plant variety 'C14-771' is provided. 'C14-771' is a commercial variety intended for the fresh market. The variety is produced from a cross of unpatented parents 'FL10-012' and 'FL05-613'.

5 Drawing Sheets

Latin name of the family, genus, and species:
Family—Ericaceae.
Genus—*Vaccinium.*
Species—*corymbosum* hybrid.
Variety denomination: The new blueberry plant claimed is of the variety denominated 'C14-771'.

BACKGROUND OF THE INVENTION

The new variety 'C14-771' was selected from a population of seedlings derived from crossing the blueberry varieties known as 'FL10-012' (unpatented seed parent) and the variety known as 'FL05-613' (unpatented pollen parent). The cross was made in 2010 in Florida, USA and the seed was sown and grown in Corindi Beach, New South Wales, Australia. The new variety was selected in 2014 from among plants located on land at Corindi Beach and assigned the breeding code 'C14-771'. Plants of 'C14-771' were propagated by cuttings for further evaluation and resulted to be uniform and stable. The new variety showed distinctive traits such as evergreen, with fruit of good size, flavor, and firmness.

SUMMARY OF THE INVENTION

The new variety 'C14-771' was originated from a cross of 'FL10-012' (unpatented seed parent) and the variety known as 'FL05-613' (unpatented pollen parent) in 2010 in Florida, USA.

The new blueberry variety resulted from seedlings produced in a controlled breeding programme. The cross was made in 2010 in Florida, USA and the seed was sown and grown in Corindi Beach, New South Wales, Australia.

The new variety was selected in 2014 from among plants located on land at Corindi Beach and has since been named 'C14-771'. Since then plants of 'C14-771' were propagated by cuttings for further evaluation and confirmed to be uniform and stable. Asexual reproduction of the new variety 'C14-771' by cutting propagation since 2014 at Corindi Beach, New South Wales, Australia has demonstrated that the new variety reproduces true to type plants.

The new variety was selected in 2014 as a single plant within a population of seedlings resulting from controlled cross of *Vaccinium* varieties. The seedling population was planted in an experimental block in the field at Corindi Beach, New South Wales, Australia and the selection of the new variety took place in the same block. Selection criteria were a combination of early to mid-season harvest, low chilling requirement, strong plant vigour, non-deciduous type of plant (evergreen), very large fruit size, good fruit flavor, and firm fruit. The new variety was subsequently evaluated for six years at the commercial farm at Corindi Beach, New South Wales, Australia.

The following characteristics of the new variety have been repeatedly observed and can be used to distinguish 'C14-771' as a new and distinct variety of *Vaccinium corymbosum* hybrid:

1. Non-deciduous (Evergreen).
2. Early to medium season crop.
3. Low chilling requirement (estimated to be between 150 and 300 hours).
4. Very large fruit size, averaging 4.2 g.

The new blueberry variety 'C14-771' has maintained its distinguished characteristics throughout successive asexual propagation. The variety has been repeatedly asexually reproduced through softwood cuttings in New South Wales, Australia and the clones are phenotypically identical to the original plant.

BRIEF DESCRIPTION OF THE DRAWINGS

The accompanying photographic illustration shows typical specimens in full color of the foliage and fruit of the new variety 'C14-771'. The colors are as nearly true as is reasonably possible in a color representation of this type.

Figure 1:
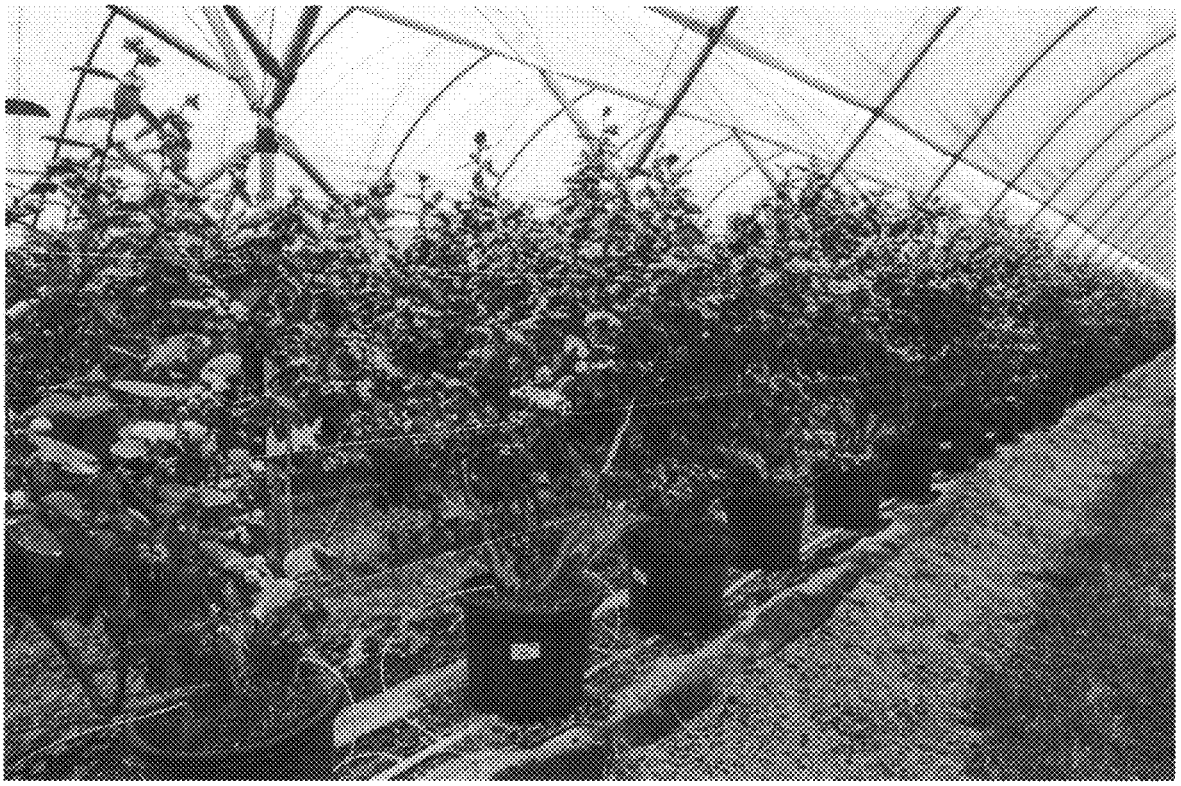
FIG. 1 is a photograph of the new variety 'C14-771', showing 3 year old plants growing in a substrate system.
Figure 2:
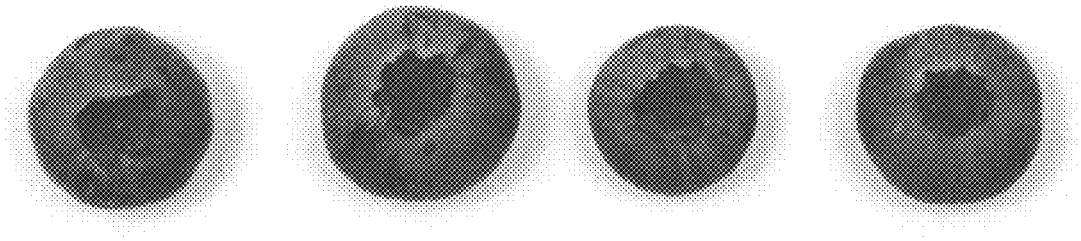
FIG. 2 is a photograph showing a typical calyx of fruit of the new variety 'C14-771'.
Figure 3:
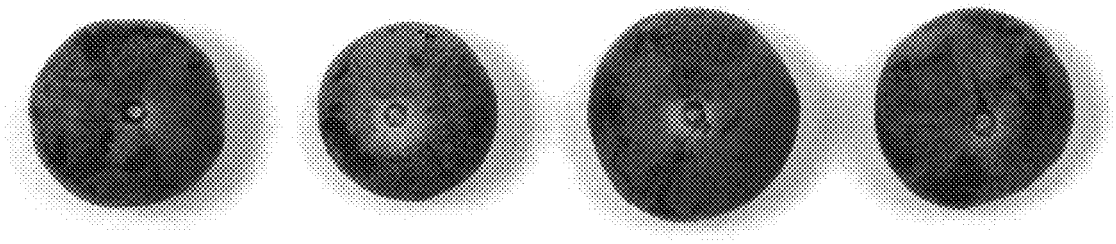
FIG. 3 is a photograph showing the typical pedicel scar of fruit of the new variety 'C14-771'.
Figure 4:
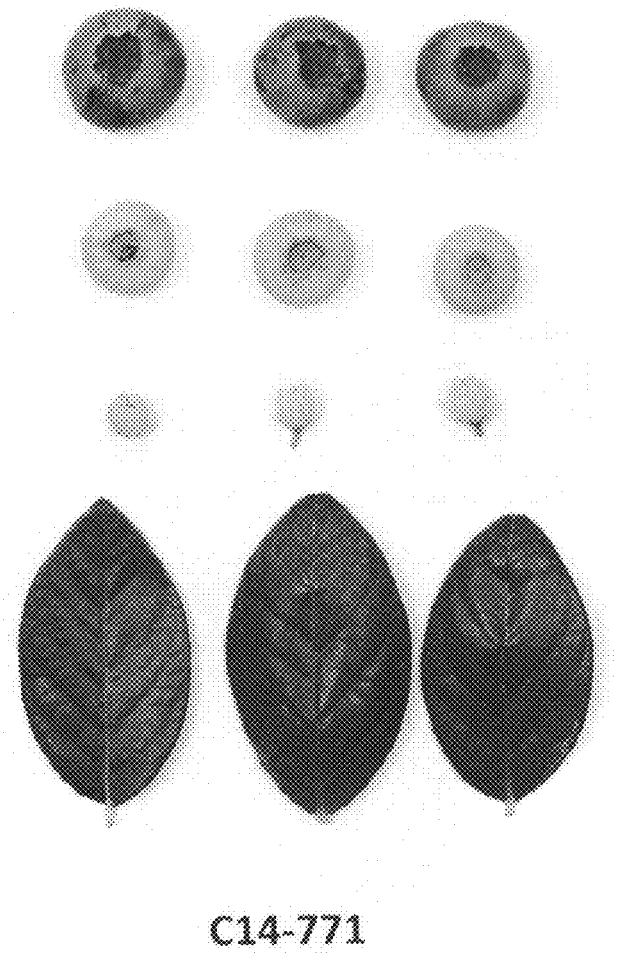
FIG. 4 is a photograph of the new variety 'C14-771' showing the botanical parts of the plants (ripe fruit, green fruit, flowers and leaves).
Figure 5:
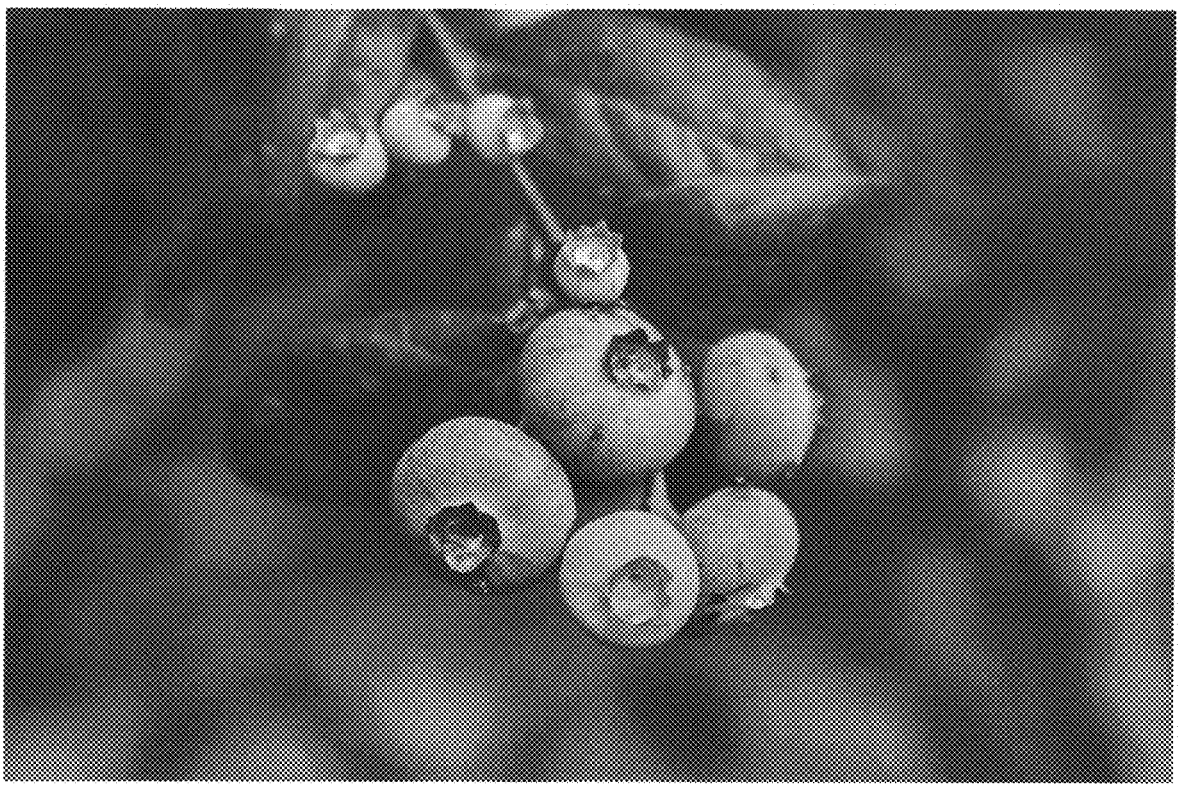
FIG. 5 is a photograph showing the large fruit size of the new variety 'C14-771'.

The colors in the photographs are as close as possible with the photographic and printing technology utilized. The color values cited in the detailed botanical description accurately describe the colors of the new blueberry variety.

DETAILED BOTANICAL DESCRIPTION

The following detailed description sets forth the distinctive characteristics of 'C14-771'. The data which defines these characteristics was collected from asexual reproductions of the original selection. Dimensions, sizes, colors, and other characteristics are approximations and averages set forth as accurately as possible. For all traits data was collected from 3 plant parts across 6 randomly selected plants. For the traits relating to fruits (e.g., fruit weight, firmness, brix, acidity) the data is an average across twenty fruits collected randomly. The plant history was taken on plants approximately 3 years of age, and the descriptions relate to plants grown in the field in Corindi Beach, New South Wales, 2456 Australia. Descriptions of fruit characteristics were made on fruit grown in Corindi Beach, New South Wales, 2456 Australia. Color designations are from the 2007 edition of The Royal Horticultural Society ("R.H.S."). 'C14-771' has not been observed under all possible environments. The phenotype may vary slightly with different growing environments such as temperature, light, fertility, soil pH, moisture and maturity levels, but without any change in the genotype.

Classification:

a. *Family*.—Ericaceae.
b. *Genus*.—*Vaccinium*.
c. *Species*.—*Corymbosum* hybrid.
d. *Common name*.—Blueberry.

Parentage:

*Female parent*.—Unpatented selection 'FL10-012'.
*Male parent*.—Unpatented selection 'FL05-613'.

Market class: Fresh market.

PLANT

General:

*Parentage*.—FL10-012 x FL05-613.
*Plant height*.—1.78 m.
*Plant width*.—1.12 m.
*Growth habit*.—Upright.
*Growth*.—Strong vigour.
*Mature cane length*.—0.88 m.
*Mature cane width*.—18.9 mm.
*Mature cane color*.—Grey-brown group, similar to 199C.
*Bark texture*.—Medium (texture between rough and smooth).
*Fruiting wood in length*.—28.0 cm.
*Productivity*.—Medium to low yield. Average of 3.1 Kg per plant (estimated equivalent production of 6.8 pounds per plant) from 3 year old plants when growing in 17 L pots at Corindi Beach, NSW. The plants are spaced at 0.7 m apart along the row and 2.5 m between the rows, which gives an estimated plant density of 5700 plants per hectare.
*Cold hardiness*.—Low chill (USDA plant hardiness Zone 4).
*Cold tolerance*.—Low.
*Chilling requirement*.—Low, estimated between 150 and 300 hours.
*Tolerance to disease*.—None assessed.
*Heat tolerance*.—Moderately resistant to heat.
*Leafing*.—Overall medium, and plant retains leaves during the winter.
*Twigginess*.—Low.

FOLIAGE

General:

*Leaf color* (*top side*).—Green group, similar to N137C.
*Leaf color* (*under side*).—Green group, similar to N138C and 138B.
*Leaf arrangement*.—Alternate.
*Leaf shape*.—Elliptic.
*Leaf margins*.—Entire.
*Leaf venation*.—Reticulate.
*Leaf length*.—Long to very long (average 72 mm).
*Leaf width*.—Broad (average 33.1 mm).
*Leaf length/width ratio*.—2.2.
*Shape of the leaf apex*.—Acute.
*Shape of the leaf base*.—Cuneate.
*Leaf nectaries*.—Absent.
*Pubescence of upper side*.—Absent.
*Pubescence of lower side*.—Absent.
*Cross sectional profile*.—Flat.
*Longitudinal profile*.—Straight.
*Attitude*.—Horizontal.

Petioles:

*Length*.—Average 4.5 mm.
*Width*.—Average 1.84 mm.
*Color*.—Yellow-green group, similar to 145B.
*Texture*.—Rough.

FLOWERS

General:

*Time of beginning of flowering*.—Early to mid-season (50% of anthesis estimated to be on the 15th of June, on 3 year old plants, cultivated at Corindi Beach, NSW).
*Flower shape*.—Urceolate.
*Flower fragrance*.—None perceptible.

Corolla:

*Shape*.—Urceolate.
*Color*.—White group, similar to NN155B.
*Length*.—7.96 mm.
*Width of widest region*.—9.6 mm.

*Diameter of corolla aperture.*—Very open, on average 5.37 mm.
*Anthocyanin coloration of corolla.*—Absent to very weak.
*Corolla ridges.*—Present.
*Petal width (ridge to ridge).*—4.64 mm.
*Protrusion of stigma.*—Very small but noticeable.
*Corolla/petal texture.*—Smooth.

Inflorescence:
*Inflorescence length (excluding peduncle).*—17.4 mm.
*Inflorescence width.*—19.24 mm.
*Inflorescence length of peduncle.*—15.6 mm.
*Flower length (excluding pedicel).*—9.96 mm.
*Flower diameter.*—8.76 mm.
*Flower length/width ratio.*—1.13.
*Surface texture of peduncle.*—Medium (between rough and smooth).
*Color of peduncle.*—Yellow-green group, similar to 145A with greyed-red group similar to 182A on top.
*Length of pedicel.*—Short, average 6.19 mm.
*Surface texture of pedicel.*—Smooth.
*Color of pedicel.*—Yellow green group, similar to 145A and 146C.
*Number of flowers per cluster.*—6.
*Flower cluster density.*—Medium.
*Flowering interval on one-year old shoot.*—July to August.
*Flowering interval on current year shoot.*—June to August.
*Number sepals per flower.*—6.
*Sepal shape.*—Deltoid.
*Shape of the sepal's apex.*—Acute.
*Margin of sepal.*—Entire.
*Texture of sepal's lower and upper side.*—Smooth.
*Color of lower side of sepal.*—Yellow green group 144C.
*Color of upper side of sepal.*—Yellow-green group 144B.

Stamen:
*Length.*—7.4 mm.
*Number per flower.*—12.
*Filament color.*—Yellow-green group, similar to 145B.

Pistil:
*Length (including ovary).*—11.2 mm.
*Style length (including stigma).*—9.3 mm.
*Style color.*—Yellow-green group, similar to 145B and N144D.

Anther:
*Length.*—4.3 mm.
*Number per flower.*—12.
*Color.*—Greyed-orange group, similar to 165B.

Pollen:
*Self compatibility.*—Yes (the variety shows a high degree of self-compatibility).
*Abundance.*—Few.
*Color.*—Yellow group, similar to 10A.

FRUIT

General:
*Time of fruit ripening.*—Early to medium.
*Cluster density.*—Medium (5-7 berries per cluster).
*Unripe fruit color.*—Light green, yellow green group, similar to 145B.
*Ripe berry color.*—Blue group 103A, when bloom is removed.
*Berry surface wax abundance.*—Medium to strong.
*Berry weight.*—Very large, on average 4.2 g.
*Berry height from calyx to scar.*—15.6 mm.
*Berry diameter.*—19.8 mm.
*Berry shape.*—Oblate.
*Fruit diameter of calyx basin.*—Medium, on average 6.6 mm.
*Fruit depth of calyx basin.*—Deep.
*Fruit stem scar.*—Medium to small and dry.
*Sweetness when ripe.*—Medium (12 Brix).
*Firmness when ripe.*—Firm, 190 g/mm, measured with FirmTech.
*Acidity when ripe.*—Medium (0.50%).
*Berry flesh color.*—Yellow-green group, similar to 145B.
*Storage quality.*—Long storage, on average 36 days.
*Suitability for mechanical harvesting.*—Not tested.
*Uses.*—Fruit to be hand harvested for fresh market.
*Self fruitfulness.*—Yes, with a proportion of the crop from parthenocarpic fruit.

SEED

General:
*Seed abundance in fruit.*—Low, on average 4 seeds per fruit.
*Seed color.*—Greyed brown group, similar to N199B.
*Seed length.*—1.66 mm.

COMPARISON BETWEEN PARENTAL AND SIMILAR CULTIVARS

Table 1 below provides a comparison between C14-771 and similar cultivars:

TABLE 1

Comparison of 'C14-771' with similar cultivars

| Characteristics | 'C14-771' | 'C99-042' (U.S. Plant Pat. No. 20,695P2) | 'Snowchaser' (U.S. Plant Pat. No. 19,503P3) |
|---|---|---|---|
| Plant vigour | Strong | Weak to medium | Medium |
| Plant growth habit | Upright | Semi-upright to intermediate | Semi-upright |
| One year old shoot length of internodes | Medium | Very short to short | Short |
| Leaf length | Long to very long | short | Long |
| Leaf length (mm) | 72 ± 2.8 | 53.10 ± 0.8 | 61.50 ± 0.9 |
| Leaf width | Broad | Very narrow to narrow | Broad |
| Leaf width (mm) | 33.1 ± 2.3 | 22.9 ± 1.3 | 34.3 ± 1.5 |
| Flower size of corolla | Medium | Medium | Medium |
| Flower corolla length (mm) | 9.3 ± 0.3 | 9.7 ± 0.3 | 9.5 ± 0.3 |
| Fruit cluster density | Medium | Sparse | Medium |
| Fruit size | Very large | Small to medium | Small to medium |
| Fruit weight (g) | 4.2 ± 0.6 | 1.9 ± 0.39 | 1.7 ± 0.21 |
| Fruit diameter (mm) | 19.8 ± 1.4 | 15.6 ± 0.96 | 15.10 ± 0.97 |
| Fruit depth of calyx basin | Deep | Medium | Shallow |
| Fruit intensity of bloom | Medium to strong | Weak to medium | Weak to medium |
| Fruit firmness | Firm | Firm | soft |
| Soluble solid content (%) | 12 | 13.1 | 14.3 |
| Titratable acidity (%) | 0.5 | 0.3 | 0.5 |
| Time of vegetative bud burst | Early | Early | Early |
| Time of beginning of flowering | Early to medium | Early to medium | Very early to early |
| Time of beginning of fruit ripening | Early to medium | Early to medium | Very early to early |

The invention claimed is:

1. A new and distinct variety of blueberry plant named 'C14-771', substantially as illustrated and described herein.

* * * * *

C14-771

C14-771